United States Patent [19]

Chang

[11] Patent Number: 5,292,517
[45] Date of Patent: Mar. 8, 1994

[54] PH SENSITIVE, REVERSIBLE GELLING, COPOLYMERIC ERODIBLE DRUG DELIVERY SYSTEM

[75] Inventor: Nienyuan J. Chang, Irvine, Calif.

[73] Assignee: Allergan, Inc., Irvine, Calif.

[21] Appl. No.: 840,875

[22] Filed: Feb. 25, 1992

[51] Int. Cl.$^5$ .................... A61K 9/08; A61K 47/32
[52] U.S. Cl. .................... 424/426; 424/428; 424/486; 424/78.33; 514/912; 514/944; 514/772.6; 523/122
[58] Field of Search .................... 424/426, 428, 78.2, 424/78.08, 484, 486; 514/912-915, 944, 772.6; 523/122; 526/271, 318.2, 936; 525/91, 327.8, 936-938, 941

[56] References Cited

U.S. PATENT DOCUMENTS

| | | | |
|---|---|---|---|
| 3,914,402 | 10/1975 | Shell | 424/32 |
| 3,956,480 | 5/1976 | Dichter et al. | 424/78.18 |
| 4,249,531 | 2/1981 | Heller et al. | 128/260 |
| 4,339,433 | 7/1982 | Kartinos et al. | 424/78.18 |
| 4,373,036 | 2/1983 | Chang et al. | 523/118 |
| 4,432,964 | 2/1984 | Shell et al. | 424/14 |
| 4,456,569 | 6/1984 | Rodson et al. | 264/4.7 |
| 4,478,818 | 10/1984 | Shell et al. | 424/14 |
| 4,569,455 | 2/1986 | Dhabar | 524/45 |
| 4,661,339 | 4/1987 | Allen et al. | 424/486 |
| 4,740,365 | 4/1988 | Yukimatsu et al. | 424/435 |
| 4,857,335 | 8/1989 | Bohm | 424/455 |
| 4,880,628 | 11/1989 | Allen et al. | 424/605 |
| 5,104,926 | 4/1992 | Russell et al. | 525/327.7 |

FOREIGN PATENT DOCUMENTS

| | | | |
|---|---|---|---|
| 0289900 | 11/1988 | European Pat. Off. | A61K 47/00 |
| 2277859 | 2/1976 | France | A61K 47/32 |
| 8906964 | 8/1989 | PCT Int'l Appl. | A61K 31/74 |

Primary Examiner—Thurman K. Page
Assistant Examiner—E. J. Webman
Attorney, Agent, or Firm—Poms, Smith, Lande & Rose

[57] ABSTRACT pH sensitive, reversible gelling erodible drug delivery compositions and methods for their production are disclosed. The compositions are liquid solutions of poly(methylvinylether/maleic acid) having pharmaceutical compounds incorporated therein. The poly(methylvinylether/maleic acid) solutions increase in viscosity with increases in pH. Thus, when the compositions are formulated at a pH lower than physiological pH's, and then delivered to a target physiological site, the liquid solution becomes viscous and adheres to the tissue for a length sufficient to provide prolonged bioavailability of the pharmaceutical compound.

15 Claims, 1 Drawing Sheet

PH SENSITIVE, REVERSIBLE GELLING, COPOLYMERIC ERODIBLE DRUG DELIVERY SYSTEM

FIELD OF THE INVENTION

The present invention relates in general to sustained release gel-like drug delivery systems. More particularly, the present invention is directed to liquid mixtures of poly(methylvinylether/maleic acid) intended for use in treating and diagnosing ocular diseases and diseases in similar physiological environments. The erodible drug delivery systems reversibly gel in response to changes in pH and adhere to mucosa making them particularly suitable for use as dropable or injectable drug delivery systems for the sustained delivery of pharmaceutical compounds.

BACKGROUND OF THE INVENTION

A problem with the administration of many pharmaceutical compounds and diagnostic compounds has been the need to retain sufficient quantities of these compounds in contact with the target tissues for a period of time sufficient to accomplish the therapeutic or diagnostic purpose. This problem is particularly acute in connection with compounds administered to the eye. In the ocular environment, tear turnover and drainage through the lacrimal system quickly remove a major portion of any compound administered directly to the eye so that only a small fraction of the original dosage remains in the eye for an extended period of time. In order to keep the pharmaceutical compound present at a therapeutic level, repeated administrations of fairly large doses are required to compensate for the loss from tear turnover and drainage. Similar problems are also encountered in connection with the nasal mucosa, oral cavity and similar physiological environments.

Early approaches to the solution of the problems associated with ocular drug delivery systems utilized semi-solid ointments or gels applied directly to the conjunctiva or cul-de-sac of the eye to retain the pharmaceutical agents contained therein on the ocular surface. Though reasonably effective at retaining adequate drug dosages in contact with the surface of the eye, a major disadvantage associated with ointments and gels is the difficulty in delivering controlled amounts. Many patients experience difficulty in applying the appropriate amount of the ointment or gel to the eye. Additionally, many of the ointments and gels cause unpleasant side effects including blurred vision and the formation of crusts around the eye and on the eyelids.

Another problem associated with the use of semi-solid gels and ointments is the tendency for many of these delivery systems to migrate within the cul-de-sac or fall completely from the eye. While some delivery systems are based upon gels which adhere to mucosa and thus have superior retention properties, many other gel systems do not meet with patient approval because of the discomfort associated with their migration.

Still another problem with many conventional gel and ointment drug delivery systems is the persistence of the gel or ointment within the ocular environment. Long after the available pharmaceutical compound is delivered, the gel or ointment can remain in the eye and continues to cause many unpleasant side effects including crusting and blurred vision. This problem is alleviated by gel drug delivery systems based on erodible gels which gradually dissolve or react to form soluble products at the physiological delivery site. However, patient dissatisfaction associated with accurately delivering recommended doses of these gels remains a problem. When attempting to deliver these gels using drop instillable methods, patients frequently apply too little or too much gel.

Another approach to controlled drug delivery is to utilize a drug loaded solid insert of a matrix material which erodes in physiological environments and simultaneously releases the incorporated drug with the erosion. One such solid insert is formulated of copolymers of a carboxylic acid such as the mono-ester of alkylvinylether/maleic acid copolymers. The ratio of acid functionalities to the number of carbon atoms in these copolymers determines the erosion rate and the drug release profile. These solid inserts function well in applications for extended release profiles. However, a significant disadvantage of these solid inserts for applications which do not require weeks or days of drug release time is the low patient acceptance associated with self-administering solid inserts. This is a particularly strong disadvantage when the inserts are intended for insertion in the ocular environment.

Alternatively, it has been proposed to utilize formulations which gel in response to changes in pH as drug delivery vehicles by carefully controlling the pH of a drug mixture, a solution which increases in viscosity upon mixing with aqueous tear fluid. Typically, these formulations are based upon polycarboxylates at concentrations as high as 10% which result in delivery systems having high buffering capacities and extended gelling times. However, these polycarboxylates have adverse effects on the chemical stability of certain pharmaceutical compounds which precludes their use in these delivery systems.

Accordingly, it is an object of the present invention to provide stable, reversibly gelling drug delivery vehicles which can be used to delivery a variety of pharmaceutical compounds to a physiological system.

It is a further object of the present invention to provide a reversibly gelling drug delivery vehicle which rapidly undergoes a viscosity change upon application to a physiological system.

It is a further object of the present invention to provide a reversibly gelling, drop-instillable drug delivery vehicle which will prolong drug contact time for improved bioavailability and sustained drug release.

It is additionally an object of the present invention to provide a delivery vehicle which is self-lubricating for patient comfort, yet which exhibits muco-adhesive properties for adhesion to mucosa.

SUMMARY OF THE INVENTION

Generally stated, the present invention accomplishes the above-described objectives by providing liquid compositions which reversibly gel in response to a variation in the pH of the liquid. More particularly, the present invention provides reversible gelling drug delivery compositions in the form of a liquid solution of poly(methylvinylether/maleic acid) copolymer and a pharmaceutically effective amount of a therapeutic or diagnostic pharmaceutical compound incorporated in the liquid solution. The poly(methylvinylether/maleic acid) copolymer is present in the liquid solution at a concentration sufficient to reversibly modify the solution viscosity in response to a variation in solution pH.

The compositions of the present invention exhibit sol-gel transitions over physiologically compatible pH ranges which make the compositions particularly well suited for use as drop-instillable drug delivery systems, as well as for use as injectable sustained release drug delivery systems. For example, drug delivery vehicles and injectable drug delivery compositions can be produced in accordance with the teachings of the present invention which exhibit free flowing viscosity ranges at a low pH of about 3, yet quickly transform to viscous gel-like compositions when exposed to physiological conditions having a pH on the order of 7.

Additionally, liquid solutions of poly(methylvinylether/maleic acid) are optically clear and exhibit bioadhesive properties making them well suited for use in the ocular environment. Once comfortably instilled in the cul-de-sac of the eye, the liquid solution of poly(methylvinylether/maleic acid) increases in viscosity and adheres to the ocular mucosa for a length of time sufficient to provide improved bioavailability of pharmaceutical compounds incorporated in the liquid solution. Exemplary compositions are formed in accordance with the teachings of the present invention from aqueous solutions of poly(methylvinylether/maleic acid) and a pharmaceutically effective amount of a therapeutic of diagnostic pharmaceutical compound. Concentrations of poly(methylvinylether/maleic acid) sufficient to reversibly modify the liquid solution viscosity in response to a variation in the mixture pH range from about 1 w/v% to about 25 w/v%. Pharmaceutically effective amounts of pharmaceutical compounds are dependent upon the type and function of the pharmaceutical compound formulated in the aqueous solution. However, exemplary compositions include pharmaceutical compounds ranging in concentration from about 0.005 w/v% to about 50 w/v%.

In contrast to prior art drug delivery vehicles, the liquid solutions of poly(methylvinylether/maleic acid) and a pharmaceutical compound exhibit improved long-term stability and pharmaceutical compound activity. Accordingly, the compositions of the present invention provide patients with easy-to-use drop instillable drug delivery compositions having an extended period of high pharmaceutical compound activity. This feature allows the drug delivery compositions of the present invention to be packaged in large ready to use configurations which can be used by patients for extended periods of time.

Further objects and advantages of the pH sensitive reversible gelling drug delivery compositions of the present invention, as well as a better understanding thereof, will be afforded to those skilled in the art from a consideration of the following detailed explanation of preferred exemplary embodiments thereof. Reference will be made to the appended sheets of drawings which will now be first described briefly.

DETAILED DESCRIPTION OF PREFERRED EMBODIMENTS

Figure 1:
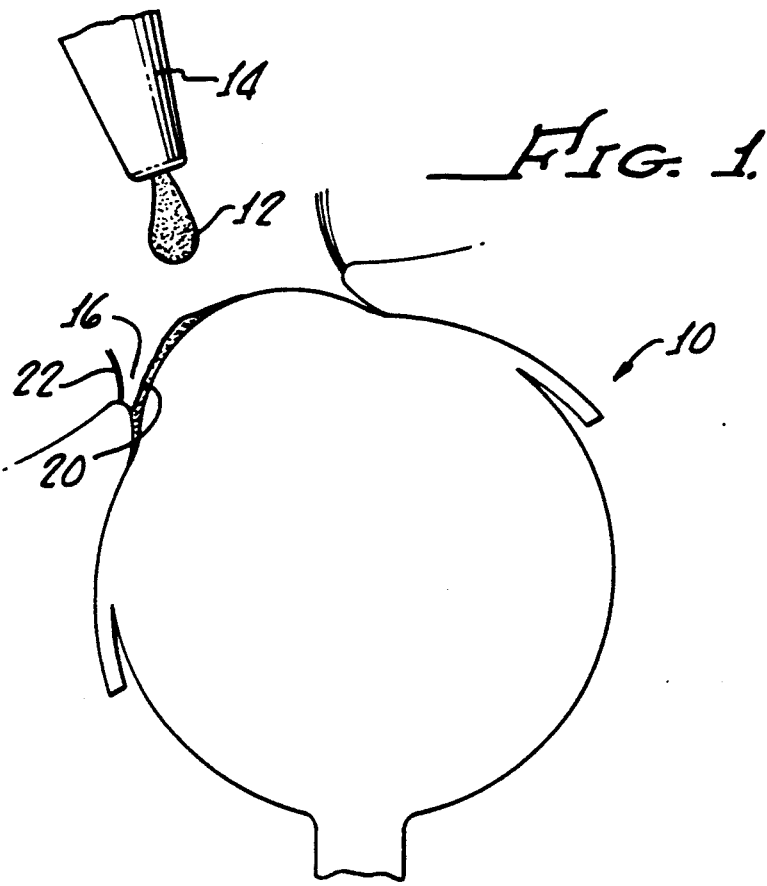
FIG. 1 is a sectional view of an eye illustrating the administration of an exemplary drop-instillable reversible gelling drug delivery composition of the present invention.

The pH sensitive reversible gelling drug delivery compositions of the present invention are primarily intended for use as drop instillable, oral and injectable drug delivery vehicles. The preferred exemplary embodiments of the present invention have viscosities and flow properties which allow them to flow freely at acidic pH's and to increase quickly in viscosity by over an order of magnitude to a gel-like consistency at physiological pH's of slightly greater than pH 7. The reversible gelling drug delivery compositions have bioadhesive properties which advantageously allow the compositions to adhere to tissue mucosa with increased drug retention time and reduced migration of the composition. For this reason, the drug delivery compositions are particularly suitable for delivering pharmaceutical compounds to the ocular environment where the adhesive properties prevent premature drainage of the compositions through the lacrimal system. Thus, for purposes of explanation and without limiting the scope of the present invention, the following exemplary embodiments will be discussed in the context of drop instillable compositions for delivering pharmaceutical compounds to the ocular environment. However, those skilled in the art will appreciate the applicability of the compositions of the present invention for delivering pharmaceutical compositions in physiological systems generally.

In its broadest capacity, an exemplary embodiment of the drug delivery compositions of the present invention which exhibits reversible changes in viscosity in response to variation in pH includes a liquid solution of poly(methylvinylether/maleic acid) at a concentration sufficient to reversibly modify the solution viscosity in response to a variation in solution pH, and incorporated in the liquid solution is a pharmaceutically effective amount of a therapeutic or diagnostic pharmaceutical compound.

Poly(methylvinylether/maleic acid) is a highly structured copolymer having the following general structure:

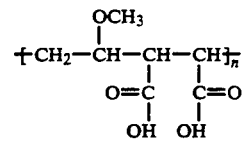

Even though the copolymer is a polycarboxylic acid in that the copolymer includes alternating repeat units of methylvinylether and maleic acid, the copolymer is typically prepared by hydrolyzing poly(methylvinylether/maleic anhydride) according to the following:

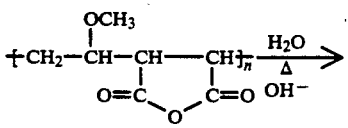

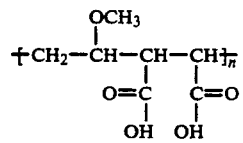

Poly(methylvinylether/maleic anhydrides) are available from GAF under the trade name GANTREZ. The polymers are also available from other commercial sources such as Polysciences and American Scientific Polymers. All exemplary embodiments described herein utilize the di-acid hydrolysis product of poly(methylvinylether/maleic anhydride) which is conveniently obtained using base catalyzed hydrolysis techniques referred to above and described more thoroughly below. Unlike prior art delivery devices and compositions which are prepared from halfesters of copolymers of maleic anhydrides or polyacrylic acids in order to obtain desired release profiles, the maleic acid copolymers are easily and completely hydrolyzed and do not depend upon controlled half-ester formation techniques which are prone to too little or too much hydrolysis.

Poly(methylvinylether/maleic anhydride) is available in molecular weights ranging from 20,000 to 100,000. Since the degree of polymerization remains the same once the poly(methylvinylether/maleic anhydride) is hydrolyzed to the di-acid, the poly(methylvinylether/maleic acid) can be produced with molecular weight similar to the parent polyanhydride compound. Those skilled in the art will appreciate that liquid solutions of higher molecular weight poly(methylvinylether/maleic acid), in general, will have higher viscosity values for any given copolymers concentration, temperature or pH. Accordingly, copolymers having any of a wide range of average molecular weights have utility in the practice of the present invention and descriptions herein of a poly(methylvinylether/maleic acid) having a specific average molecular weight is exemplary and nonlimiting.

Liquid solutions of poly(methylvinylether/maleic acid) incorporating a pharmaceutical compound exhibit increases in solution viscosity in response to an increase in solution pH. Typically, the variation in solution ph is between less than a pH of 4 nd greater than a pH of 5. Thus, for example, aqueous solutions of about 2 w/v% poly(methylvinylether/maleic acid), formulated at a pH of about 3, will increase in viscosity from about 220 cps to about 3680 cps when the ph of the aqueous solution is increased to about 7. In terms of their usefulness for physiological environment applications, the compositions of the present invention can be formulated at a relatively low pH and then delivered to a tissue site, where within 1 to 2 minutes, the solutions quickly increase in viscosity to a gel-like consistency as the result of exposure to a higher physiological pH. Exposure to increasingly higher pH's causes the poly(methylvinylether/maleic acid) to deprotonate with a simultaneous unwinding of the polymeric chain and increased resistance to flow which is attributed to the increased polymeric volume. As those skilled in the art will appreciate, compatible pharmaceutical compounds incorporated into the poly(methylvinylether/maleic acid) liquid solutions will be entrapped in the viscous composition and the increased viscosity further reduces migration and loss of the compositions to natural fluid turnover within the tissue environment. Combined with the non-irritating and tissue adhesive properties of the poly(methylvinylether/maleic acid) solution, the compositions of the present invention provide a vehicle for the prolonged release and increased bioavailability of pharmaceutical compound incorporated in the liquid solution of poly(methylvinylether/maleic acid).

For compositions exhibiting viscosity ranges suitable for self-administering liquid drops which form gel-like deliver vehicles, effective viscosity modifying concentrations of poly(methylvinylether/maleic acid) range from about 1 wt% to about 25 wt%. By varying the concentration ranges of poly(methylvinylether/maleic acid) a wide range of viscosities and degree of viscosity changes can be produced. Preferred exemplary embodiments include aqueous solutions of from about 2 w/v% to about 10 w/v% poly(methylvinylether/maleic acid). Thus aqueous solutions of 2 w/v% poly(methylvinylether/maleic acid) formulated at pH 3 have a viscosity of 220 cps measured at a shear rate of 0.28 1/sec. When the pH of the aqueous solution is raised to 7.1 the viscosity increases to about 3700 cps. Similarly, aqueous solutions of 8 w/v% poly(methylvinylether/maleic acid) formulated at pH 3 have a viscosity of 3100 cps. When the solution pH is increased to only 5 the viscosity of the 8 w/v% poly(methylvinylether/maleic acid) increases to 34,200 cps.

Pharmaceutical compounds suitable for incorporating into the liquid solutions of poly(methylvinylether/maleic acid) at pharmaceutically effective concentrations include a wide variety of compatible medicaments including antibacterials, antihistaminics, antiinflammatories, miotics, anticholinergics, mydriatics, antiglaucoma compounds, antiparasitic compounds, antivirals, carbonic anhydrase inhibitors, anti-fungal agents, anesthetic agents, peptides, proteins, diagnostic agents, lubricants and immunosuppressive agents.

As those skilled in the art will appreciate, the above mentioned classes of pharmaceutical compounds are exemplary only. Because the drug delivery compositions of the present invention are uniquely suited for utilization in a wide variety of physiological applications including ocular, oral nasal, rectal or subcutaneous administration of pharmaceutical compounds, a wide variety of pharmaceutical agents may be incorporated in the liquid solutions of poly(methylvinylether/maleic acid).

Preferred exemplary embodiments of the present invention include aqueous soluble pharmaceutical compounds, although, non-soluble medicaments which are incorporated in particulate form are also contemplated to be within the scope of the present invention. Thus, liquid solutions of from 1 wt% to 25 wt% poly(methylvinylether/maleic acid) incorporating from about 0.005 wt% to 50 wt% of a soluble or dispersed pharmaceutical compound provide drug delivery vehicles for delivering pharmaceutically effective amounts of medicament over a period of less than one hour to several hours when delivered to a tissue target site.

A preferred pharmaceutical compound for incorporating into aqueous solutions of poly(methylvinylether/maleic acid) is dipivalyl epinephrine hydrochloride (DPE). In addition to providing a very effective means for prolonged administering of DPE to the ocular environment, aqueous solutions of DPE surprisingly provide a medium which contributes to an increased long term storage and chemical stability of this pharmaceutical compound over prior art delivery vehicles. The reason for the increased stability is not completely known, however, it is believed it is related to the structured nature of the poly(methylvinylether/maleic acid). That is, the methylvinyl ether and maleic acid units predictably repeat in an ABABAB pattern with two carboxylic acid functionalities positioned in close proximity for complexing and/or chelating with the DPE. This is in contrast to the polyacrylic acid polymers and copolymers which are produced to form random polymers and copolymers with little structural predictability.

As a result of the long term stability of the compositions of the present invention, they can be prepared, stored and finally administered to a tissue site without additional patient handling. As a result, ready-to-use multiple packaging can be employed effectively when preparing and administering these drug delivery vehicles through a variety of administration routes such as injection or dropable liquids or sprays. Processes for delivery of pharmaceutical compounds to physiological sites having a pH of at least 5 include the steps of providing a liquid solution of poly(methylvinylether/maleic acid) and at least one pharmaceutical compound incorporated in the liquid solution and then introducing the liquid solution to the physiological site. The liquid solution is formulated to a pH of between about 1 and 4 and quickly increases in viscosity when exposed to a pH of at least 5.

Figure 2:
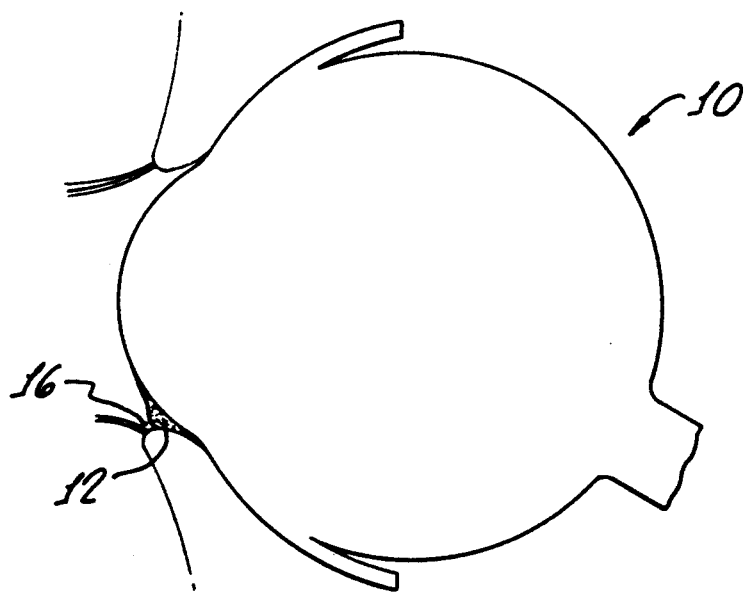
FIG. 2 is a sectional view of an eye illustrating the drug delivery composition of the present invention residing in the cul-de-sac of the eye following gelation.

While the drug delivery compositions of the present invention are useful for administering drugs to a variety of tissue sites, they are particularly suitable for delivering drug to the ocular environment, a process which is generally illustrated in FIG. 1 and 2. More specifically, FIG. 1 illustrates a vertical section view of an eye 10 having a lower cul-de-sac 16 formed by the conjunctiva 20 and the lower eyelid 22. The eye 10 of FIG. 1 is receiving a low viscosity liquid drop 12 of the drug delivery composition of the present invention from an eye dropper type device 14. Following administration to the ocular environment site, the liquid drop 12 of poly(methylvinylether/maleic acid is immediately exposed to physiological pH's on the order of about 7. This change in pH causes the liquid drop to rapidly gel to a viscous, bioadhesive form as shown in FIG. 2, a vertical section view of an eye 10 illustrating the liquid drop 12. Following gelation, the drop 12 remains in its delivery position within the lower cul-de-sac 16 of the eye 10 with a minimum of patient discomfort. The size of the liquid drop 12 preferably ranges from approximately 20 μl to 50 μl, with 25 μl drops being particularly preferred. Thus, from one drop of the liquid compositions which contains about 25 μl of solution, a recipient receives from about 0.0025 mg to about 12.5 mg of pharmaceutical compound.

The compositions of the present invention can be prepared and sterilized by simply dissolving the appropriate amount of poly(methylvinylether/maleic acid) and pharmaceutical compound in a selected volume of sterile water using sterile fill techniques. Due to their relatively low viscosities at the formulated pH, advantageously, poly(methylvinylether/maleic acid) solution incorporating soluble pharmaceutical compounds can be sterile filtered using filters with effective pore sizes of less than 0.4 micrometers without the need to utilize high pressure flow systems to force the compositions through the filters. When insoluble pharmaceutical compounds with particulates larger than sterile filter pore size are utilized, standard sterile fill techniques can be carried out easily.

While the compositions of the present invention, when formulated at the desired low pH, have osmolalities within physiological ranges of 200 mOs to 500 mOs, inorganic or organic additives can also be incorporated in order to adjust the osmolality of the composition. Thus, inorganic salts such as sodium chloride and potassium chloride or organic compounds such as any of a large variety of sugars can be incorporated in the compositions of the present invention when desired.

The following non-limiting examples are offered as being illustrative of the properties of exemplary compositions of the present invention. In the following examples, concentrations are expressed in weight per volume percent (w/v%) and all viscosity measurements were obtained at 25° C.

EXAMPLE 1

Poly(methylvinylether/maleic acid) was obtained by hydrolyzing poly(methylvinylether/maleic anhydride) according to the following procedure. A 10 g sample of poly(methylvinylether/maleic anhydride) obtained from GAF and having an average molecular weight of 80,000 was slowly added, with agitation, to 125 ml water at 90° C. The polymer and water mixture was stirred for 30 minutes while the polymer slowly dissolved in the water. The aqueous solution of poly(methylvinylether/maleic anhydride) was then cooled to about 25° C. and the pH was adjusted to about 9 by adding 0.1 N NaOH. The polymer was allowed to hydrolyze over a period of 24 hours while maintaining the pH at 9 using a Radiometer pH titration meter with mild agitation.

EXAMPLE 2

The viscosity characteristics of aqueous solutions of 8 w/v% poly(methylvinylether/maleic acid) were determined as follows. The pH of the 8 w/v% aqueous solution prepared in Example 1 above was adjusted to 1.7 by adding 1.0 N HCl and then measuring the solution viscosity with a Carri-Med C.S. cone-and-plate rheometer at 0.28 1/sec shear rate. The pH of the poly(methylvinylether/maleic acid) solution was then successively increased to 3.05, 3.95, and 5.0 with the addition of 1.0 NaOH. The solution viscosity at each of these pH's was measured using the same instrument under the same conditions. Table I illustrates the increase in viscosity characteristic of a 8 w/v% aqueous solution of poly(methylvinylether/maleic acid)

TABLE I

| Viscosities of 8 w/v % aqueous solutions of poly(methylvinylether/maleic acid) (80,000 molecular weight) at 0.28 1/sec and 25° C. ||
|---|---|
| pH | viscosity (cps) |
| 1.7 | 1,500 |
| 3.05 | 3,100 |
| 3.95 | 18,300 |
| 5.0 | 34,200 |

EXAMPLE 3

A 2 w/v% aqueous solution of poly(methylvinylether/maleic acid) was obtained by hydrolyzing poly(methylvinylether/maleic anhydride) from GAF having a molecular weight of 67,000 as described in Example 1 above. The pH was varied with the appropriate addition of 1.0 N HCl or 1.0 N NaOH also as described above. After each addition of acid or base the solution viscosity was measured using the Carri-Med cone-and-plate rheometer at a shear rate of 0.28 1/sec. As illustrated in Table II, the lower concentrations of poly(methylvinylether/maleic acid) as well as the slightly lower average molecular weight result in aqueous solutions having somewhat lower viscosities and less pronounced changes in viscosities with changes in pH.

TABLE II

Viscosities of 2 w/v % aqueous solutions of poly(methylvinylether/maleic acid) (67,000 molecular weight) at 0.28 1/sec and 25° C.

| pH | viscosity (cps) |
| --- | --- |
| 2.0 | 167 |
| 3.0 | 219 |
| 4.1 | 2,200 |
| 6.0 | 3,720 |
| 7.1 | 3,680 |

EXAMPLE 4

A 5 w/v% aqueous solution of poly(methylvinylether/maleic acid) was prepared by dissolving 10 g or the polymer prepared in Example 3 above in 200 ml of water. Then 0.4 g of levo-bunolol hydrochloride was added to the solution resulting in a drug concentration of 0.2 w/v%. The viscosity characteristics of the drug and co-polymer solution at various pH's were determined by adjusting the pH with appropriate amounts of 1.0 N NaOH or 1.0 N HCl and then measuring the solution viscosity with a Carri-Med cone-and-plate rheometer at a shear rate of 0.28 1/sec. Table III, details the results of these measurements and also illustrates the almost 30 fold increase in viscosity resulting in an increase in pH from 2.3 to 7.4.

TABLE III

Viscosities of 5 w/v % aqueous solutions of poly(methylvinylether/maleic acid) (67,000 molecular weight) incorporating 0.2 w/v% levo-bunolol hydrochloride at 0.28 1/sec and 25° C.

| pH | viscosity (cps) |
| --- | --- |
| 2.3 | 260 |
| 3.1 | 330 |
| 3.5 | 2,540 |
| 4.6 | 6,700 |
| 6.0 | 7,100 |
| 7.4 | 6,750 |

EXAMPLE 5

The tissue compatibility and toxicity characteristics of aqueous solution of poly(methylvinylether/maleic acid) were examined by first preparing a 5 w/v% solution of 67,000 poly(methylvinylether/maleic acid). Then a 35 μL drop of the polymer solution was drop instilled in the left eye of each of 24 female New Zealand Albino rabbits. As a control, the right eye of each rabbit was dosed with a 35 μL drop of normal saline solution. The rabbits's eyes were examined with a slit lamp for cornea hazing and staining as well as by visual observation for any signs of irritation. The regimen of dosing was repeated three times at one-hour intervals in conjunction with the examination. Results indicated that aqueous solutions poly(methylvinylether/maleic acid) are neither irritating nor toxic nor cytotoxic to rabbit corneas.

EXAMPLE 6

The tissue compatibility and toxicity characteristics of aqueous solution of poly(methylvinylether/maleic acid) were examined by first preparing a 10 w/v% solution of 80,000 poly(methylvinylether/maleic acid). Then a 35 μL drop of the polymer solution was drop instilled in the left eye of each of 24 female New Zealand Albino rabbits. As a control, the right eye of each rabbit was dosed with a 35 μL drop of normal saline solution. The rabbits's eyes were examined with a slit lamp for cornea hazing and staining as well as by visual observation for any signs of irritation. The regimen of dosing was repeated three times at one-hour intervals in conjunction with the examination. Results indicated that 10 w/v% aqueous solutions poly(methylvinylether/maleic acid) are neither irritating nor toxic nor cytotoxic to rabbit corneas.

EXAMPLE 7

In order to determine the stability of aqueous solutions of poly(methylvinylether/maleic acid) incorporating dipivalyl epinephrine hydrochloride (DPE) the following tests were carried out. A 2 w/v% aqueous solution of poly(methylvinylether/maleic acid (molecular weight of 70,000) and 0.1 w/v% DPE (Sample A) was stored at 45° C. for 28 days. A control sample of an aqueous solution of 0.1 w/v% DPE (SAMPLE B) was also stored at 45° C. for 28 days. The pH of both samples was adjusted to 3.5 with 0.1 N HCl.

Sample A and Sample B were periodically analyzed for DPE concentration using high performance liquid chromatography. The results of these analyses are tabulated in Table IV.

TABLE IV

| Time (day) | % DPE Remaining in Sample | |
| --- | --- | --- |
| | Sample A | Sample B |
| 0 | 100% | 1005 |
| 1 | 94 | 100 |
| 2 | 97 | 101 |
| 7 | 95 | 99 |
| 14 | 98 | 92 |
| 28 | 99 | 87 |

The results of DPE concentration analyses shown in Table Iv indicate that the shelf stability of DPE is enhanced in the presence of poly(methylvinylether/maleic acid). Supporting this conclusion is the observation that Sample A remains colorless while Sample B exhibits a color change. This color change is attributed to a DPE degradation product, adrenochrome, which is known to be colored.

EXAMPLE 8

In order to determine the ability of aqueous solutions of poly(methylvinylether/maleic acid) to maintain a consistent molecular weight and viscosity characteristic over time the following tests were performed. A 5 w/v% aqueous solution of 67,000 molecular weight poly(methylvinylether/maleic acid) was prepared by dissolving 10 g of the polymer in 200 ml water. The pH of the solution was adjusted to 3.5 by adding 0.1 N HCl. The polymer solution was then stored at ambient temperatures for three months. Following the storage period a static light scattering technique and FTIR analysis techniques were utilized to determine the polymer's molecular weight as well as its chemical characteristics. No change in either molecular weight or chemical functionalities were observed.

At the end of the storage period, the pH of the polymer solution was varied with the appropriate addition of 0.1 N HCl or 1.0 N NaOH. The viscosity of the polymer solution at a number of different pH's was measured using a Carri-Med cone-and-plate rheometer at a shear rate of 0.28 1/sec. Table V details the viscosity values obtained for a solution having a 5 w/v% polymeric carrier component at each pH. When compared with the values obtained for a solution having an equivalent polymeric carrier component with 0.2 w/v% levo-bunolol hydrochloride in Example 4, it is evident that the viscosity value imparted by a polymeric carrier component at each pH remains stable.

TABLE V

Viscosities of 5 w/v % aqueous solutions of poly(methylvinylether/maleic acid) (67,000 molecular weight) after 3 months storage at ambient temperatures measured at 0.28 1/sec and 25° C.

| pH | viscosity (cps) |
|---|---|
| 2.1 | 220 |
| 3.3 | 375 |
| 3.9 | 4,240 |
| 4.6 | 5,800 |
| 6.0 | 6,900 |
| 7.4 | 6,450 |

Having thus described preferred exemplary embodiments of the present invention, it should be noted by those skilled in the art that the disclosures herein are exemplary only and that alternative, adaptations and modifications may be made within the scope of the present invention. Accordingly, the present invention is not limited to the specific embodiments illustrated herein.

I claim

1. A reversible gelling drug delivery composition exhibiting a change in solution viscosity in response to variations in pH value, said composition comprising:
   an aqueous solution of from about 1 w/v% to about 25 w/v% poly(methylvinylether/maleic acid) having a number-averaged molecular weight of from about 20,000 to about 100,000 and from about 0.005 w/v% to about 50 w/v% of a therapeutic or diagnostic pharmaceutical compound, said aqueous solution having a formation pH value of from about 1–4 and said therapeutic or diagnostic pharmaceutical compound being chemically stable in the presence of said poly(methylvinylether/maleic acid).

2. The reversible gelling drub delivery composition of claim 1 wherein said aqueous solution reversibly gels at a pH value between about 5–8.

3. The reversible gelling drug deliver composition of claim 1 wherein the solution formation viscosity of said composition is between about 50 cps and about 34,000 cps at 25° C.

4. The reversible gelling drug delivery composition of claim 1 wherein said poly(methylvinylether/maleic acid) is present at a concentration of from about 2 w/v% to about 10 w/v%.

5. The reversible gelling drub delivery composition of claim 1 wherein said therapeutic or diagnostic pharmaceutical compound is present at a concentration of from about 0.05 w/v% to about 0.5 w/v%.

6. The reversible gelling drug delivery composition of claim 1 wherein said therapeutic or diagnostic pharmaceutical compound is selected from the group consisting of antibacterials, antiinflammatories, miotics, anticholinergics, antiglaucoma compounds, antiparasitic compounds, carbonic anhydrase inhibitors, anesthetic agents, peptides, proteins, diagnostic agents and immunosuppressive agents.

7. The reversible gelling drug delivery composition of claim 1 wherein said therapeutic or diagnostic pharmaceutical compound is selected from the group consisting of dipivalyl epinephrine and levo-bunolol.

8. The reversible gelling drub delivery composition of claim 1 wherein said therapeutic or diagnostic pharmaceutical compound is present at a concentration of from about 0.1 w/v% to about 0.2 w/v%.

9. The reversible gelling drug delivery composition of claim 1 wherein said therapeutic or diagnostic pharmaceutical compound is selected from the group consisting of antihistaminics, mydriatics, antivirals, and anti-fungal agents.

10. A pH sensitive reversible gelling drug delivery composition comprising:
    an aqueous solution of from about 2 w/v% to about 10 w/v% poly(methylvinylether/maleic acid) copolymer having a number-averaged molecular weight of from about 20,000 to about 100,000; and from about 0.05 w/v% to about 0.5 w/v% dipivefrin, said aqueous solution having a formation pH value of from about 1–4.

11. A process for delivering a therapeutic or diagnostic pharmaceutical compound over an extended period of time to a mammalian physiological site having a pH value of at least about 6, said process comprising the steps of:
    providing an aqueous solution of from about 1 w/v% to about 25 w/v% poly(methylvinylether/maleic acid) having a number-averaged molecular weight from about 20,000 to 100,000 and from about 0.005 w/v% to about 50 w/v% of a therapeutic or diagnostic pharmaceutical compound, said aqueous solution having a pH value of between about 1–4 and said therapeutic or diagnostic pharmaceutical compound being chemically stable in the presence of said poly(methylvinylether/maleic acid); and
    introducing said aqueous solution to said mammalian physiological site.

12. The process of claim 11 wherein said therapeutic or diagnostic pharmaceutical compound is present at a concentration of from about 0.05 w/v% to about 0.5 w/v%.

13. The process of claim 11 wherein said therapeutic or diagnostic pharmaceutical compound is selected from the group consisting of dipivalyl epinephrine and levo-bunolol.

14. The processing claim 11 wherein said poly(methylvinylether/maleic acid) is present in said aqueous solution at a concentration of from about 2 w/v% to about 10 w/v%.

15. The process of claim 11 wherein said introducing step comprises applying drop-sized aliquots of said aqueous solution to said mammalian physiological site.

* * * * *